United States Patent
Yang et al.

(10) Patent No.: US 10,470,905 B2
(45) Date of Patent: Nov. 12, 2019

(54) BALLOON CATHETERS AND METHODS FOR USE

(71) Applicant: Ostial Corporation, Sunnyvale, CA (US)

(72) Inventors: Yi Yang, San Francisco, CA (US); Jake Wolenberg, Santa Clara, CA (US); Archimedes Sanati, Sunnyvale, CA (US); Fred H. Co, Santa Clara, CA (US); Farhad Khosravi, Los Altos Hills, CA (US)

(73) Assignee: OSTIAL CORPORATION, Campbell, CA (US)

( * ) Notice: Subject to any disclaimer, the term of this patent is extended or adjusted under 35 U.S.C. 154(b) by 8 days.

(21) Appl. No.: 15/470,810

(22) Filed: Mar. 27, 2017

(65) Prior Publication Data

US 2018/0214289 A1    Aug. 2, 2018

Related U.S. Application Data

(60) Provisional application No. 62/313,666, filed on Mar. 25, 2016.

(51) Int. Cl.
*A61M 29/02* (2006.01)
*A61F 2/958* (2013.01)
*A61M 25/10* (2013.01)
*A61F 2/82* (2013.01)

(52) U.S. Cl.
CPC ............. *A61F 2/958* (2013.01); *A61M 25/10* (2013.01); *A61M 25/104* (2013.01); *A61M 29/02* (2013.01); *A61F 2002/821* (2013.01); *A61M 2025/1068* (2013.01); *A61M 2025/1084* (2013.01)

(58) Field of Classification Search
CPC .. A61F 2/958; A61F 2/24; A61F 2/954; A61F 2002/821; A61M 25/10; A61M 2025/1068; A61M 2025/1084; A61M 2025/1043
See application file for complete search history.

(56) References Cited

U.S. PATENT DOCUMENTS

2013/0060316 A1 * 3/2013 Sanati .................... A61F 2/954
623/1.11

* cited by examiner

Primary Examiner — George J Ulsh
(74) Attorney, Agent, or Firm — William A. English; Vista IP Law Group LLP

(57) ABSTRACT

Apparatus and methods are provided for flaring a stent deployed within a branch vessel including an ostium communicating with a main vessel, a first end of the stent extending at least partially from the branch. A catheter is provided that includes a balloon having a reinforced region adjacent an unreinforced region. When the balloon is positioned at a desired location, e.g., within a stent, prosthetic valve, or other tubular prosthesis, the balloon may be inflated to a first pressure causing the reinforced and unreinforced regions to expand substantially simultaneously. Upon inflation of the balloon beyond the first pressure, the reinforced region of the balloon remains at the first diameter and the unreinforced region continues to expand, e.g., to flare one or more ends of the prosthesis.

16 Claims, 6 Drawing Sheets

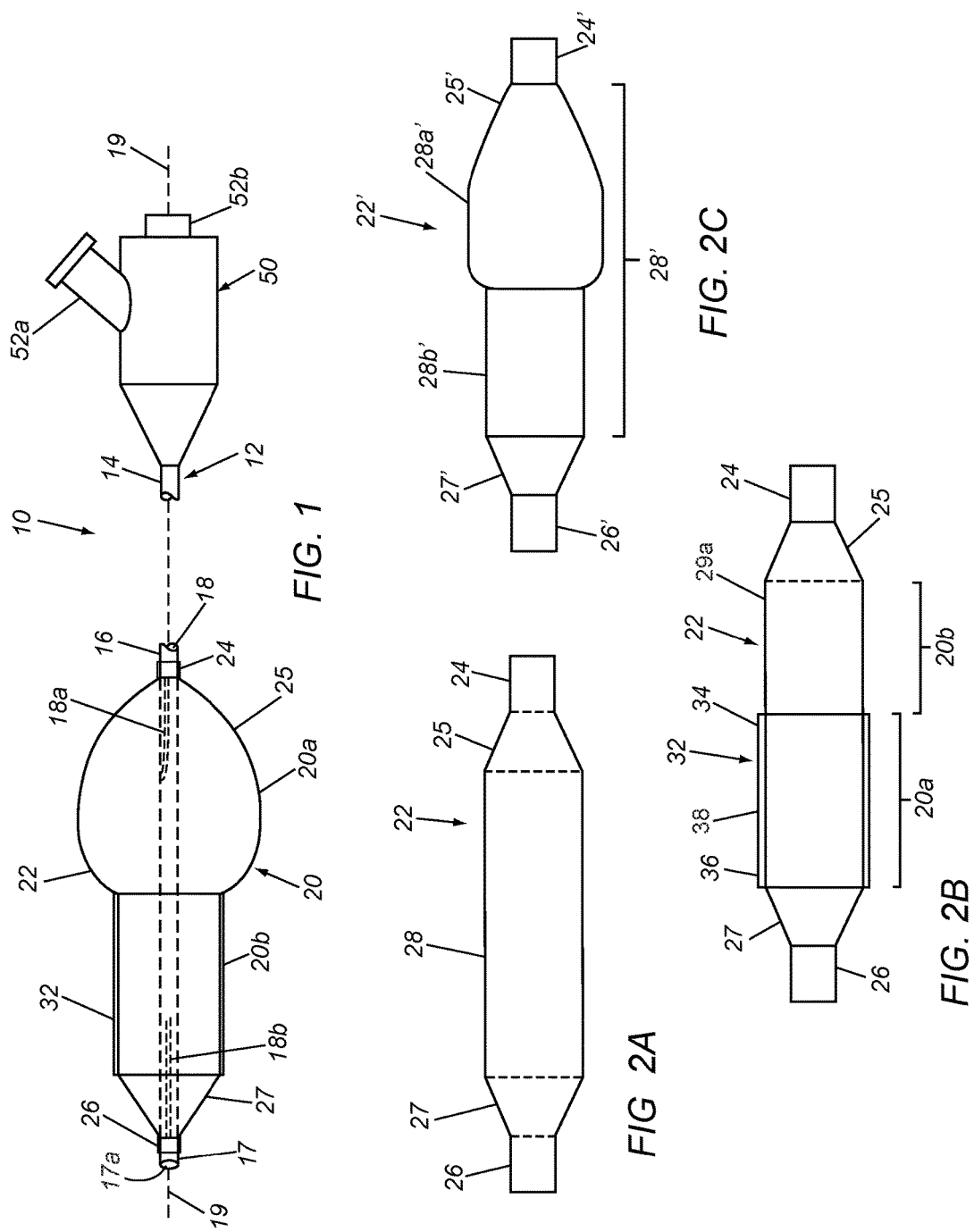

BALLOON CATHETERS AND METHODS FOR USE

The present application claims benefit of provisional application Ser. No. 62/313,666, filed Mar. 25, 2016, the entire disclosure of which is expressly incorporated by reference herein.

FIELD OF THE INVENTION

The present invention relates generally to apparatus and methods for treating stenoses, occlusions, or other lesions within a body lumen, such as an artery or other blood vessel, and, more particularly, to apparatus and methods for flaring or otherwise expanding stents, prosthetic valves, or other prostheses deployed within a body lumen, such as a branch vessel including an ostium extending from a main vessel or trunk.

BACKGROUND

Tubular endoprosthesis or "stents" have been suggested for dilating or otherwise treating stenoses, occlusions, and/or other lesions within a patient's vasculature or other body lumens. For example, a self-expanding stent may be maintained on a catheter in a contracted condition, e.g., by an overlying sheath or other constraint, and delivered into a target location, e.g., a stenosis within a blood vessel or other body lumen. When the stent is positioned at the target location, the constraint may be removed, whereupon the stent may automatically expand to dilate or otherwise line the vessel at the target location. Alternatively, a balloon-expandable stent may be carried on a catheter, e.g., crimped or otherwise secured over a balloon, in a contracted condition. When the stent is positioned at the target location, the balloon may be inflated to expand the stent and dilate the vessel.

Vascular stenoses, e.g., within arteries supplying the heart, can lead to hypoflow conditions in the vessel, which may cause ischemia and/or infarction of the organ being supplied by that vessel, e.g., the heart. Sometimes, a stenosis or other lesion may occur at an ostium or bifurcation, i.e., where a branch vessel extends from a main vessel or trunk. In such situations, it may be difficult to visualize the lesion and/or accurately position a stent within the ostium and/or branch vessel.

Often, when the stent is deployed in such anatomy, one end of the stent may extend out from the ostium into the main vessel, e.g., into the aorta from a coronary artery, common carotid artery, or peripheral artery. Such a position of the stent may cause difficulty in future endoluminal interventions, e.g., reentering the branch vessel, which may require recrossing the stent. In addition, there may be risk that the end of the stent extending from the ostium may cause damage to neighboring structures, such as aortic valve leaflets adjacent to the ostium of a coronary vessel. Furthermore, there may be little or no contact between the stent and the wall of the ostium, which may result in suboptimal treatment of the lesion.

To address these problems, it has been suggested to over-expand or flare the end of the stent extending into the main vessel, e.g., to direct the end of the stent against or closer to the wall of the ostium. Thereafter, it may be easier to recross the stent in case future endovascular study or intervention is required. In addition, in the case of coronary stents, flaring the end of the stent extending into the aorta may also move the end further from the aortic lumen and decrease the risk of damage to the aortic leaflets. Furthermore, direct contact or closer positioning of the stent to the wall of the ostium may result in improved treatment of the lesion.

Accordingly, apparatus and methods for flaring and/or otherwise expanding stents or other prostheses would be useful.

SUMMARY OF THE INVENTION

The present invention is directed to apparatus and methods for treating stenoses, occlusions, or other lesions within a body lumen, such as an artery or other blood vessel. More particularly, the present invention is directed to apparatus and methods for flaring and/or otherwise expanding stents, prosthetic valves, or other prostheses deployed within a body lumen, such as a stent deployed within a branch vessel including an ostium extending from another main vessel or trunk.

In accordance with one embodiment, an apparatus is provided for flaring a stent, prosthetic valve, or other prosthesis that includes a tubular member comprising a proximal end, a distal end sized for introduction into a patient's body, and one or more lumens extending therebetween; and a balloon carried on the distal end. The balloon includes a first membrane including first and second ends attached to the distal end, and a central region extending between the first and second tapered regions transitioning to the first and second ends, respectively; and a second membrane surrounding the central region from the second tapered region partially towards the first tapered region to define a reinforced region of the balloon, wherein the first membrane is formed from elastic material and the second membrane is formed from material having an elasticity equal to or less than the first membrane.

In accordance with another embodiment, an apparatus is provided for flaring a stent that includes a tubular member comprising a proximal end, a distal end sized for introduction into a patient's body, and one or more lumens extending therebetween; and a balloon carried on the distal end. The balloon includes a first membrane including first and second ends attached to the distal end, and a central region extending between the first and second tapered regions transitioning to the first and second ends, respectively; and a second membrane surrounding a portion of the central region spaced apart from the first and second tapered regions to define a reinforced central region of the balloon, wherein the first membrane is formed from elastic material and the second membrane is formed from material having an elasticity equal to or less than the first membrane.

In accordance with still another embodiment, a method is provided for flaring a prosthesis previously deployed within a patient's body that includes providing an elongate member including a proximal end, a distal end, a balloon on the distal end including a first elastic membrane and a second membrane on a reinforced region of the first membrane adjacent an unreinforced region; introducing the distal end into body lumen adjacent a prosthesis with the balloon in a contracted condition; positioning the balloon through the prosthesis such that the reinforced region is disposed within the prosthesis; initially inflating the balloon to expand both the unreinforced region to a first diameter such that the reinforced region engages the prosthesis with the reinforced region; and further inflating the balloon such that the unreinforced region continues to expand to flare one end of the prosthesis while the reinforced region of the balloon remains at the first diameter.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is a side view of an exemplary embodiment of a catheter including a balloon having a first region and a second reinforced region to control expansion of the balloon.

FIGS. 2A and 2B show an exemplary method for manufacturing a balloon, such as the balloon on the catheter of FIG. 1, from first and second membranes.

FIG. 2C is a side view of an alternative embodiment of a first membrane that may be used to make a balloon, such as the balloon on the catheter of FIG. 1.

DETAILED DESCRIPTION OF THE EXEMPLARY EMBODIMENTS

Figure 2D:
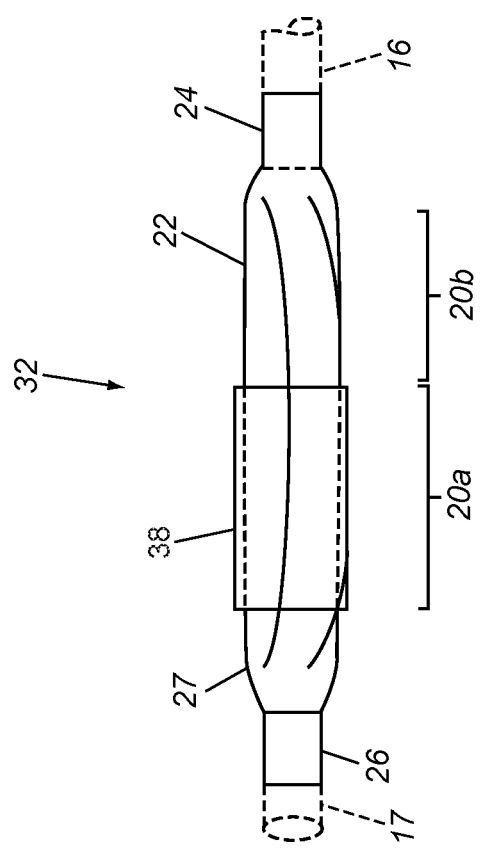
FIG. 2D shows the balloon of FIGS. 1 and 2B rolled or folded over a distal end of the catheter into a delivery condition.

Turning to the drawings, FIG. 1 shows an exemplary embodiment of an apparatus 10 for flaring and/or otherwise expanding a stent or other prosthesis (not shown), e.g., within or adjacent an ostium or other bifurcation between a main lumen and a branch lumen (also not shown). Generally, the apparatus 10 includes a catheter or other elongate tubular member 12 having a proximal end 14, a distal end 16, and one or more lumens 18 extending between the proximal and distal ends 14, 16, thereby defining a longitudinal axis 19 extending between the proximal and distal ends 14, 16.

As shown, the catheter 12 may include a balloon or other expandable member 20 on the distal end 16, e.g., including multiple regions for flaring and/or otherwise expanding a stent, prosthetic valve, or other tubular prosthesis previously deployed within a body lumen (not shown), as described further below. In addition, the distal end 16 may include one or more markers, e.g., one or more bands of radiopaque material (not shown), to facilitate positioning the catheter 12 relative to a stent and/or anatomical structures within a patient's body. Optionally, the apparatus 10 may be provided as a kit or system including one or more additional components, such as syringe, a guide catheter, and/or one or more guidewires (not shown).

The catheter 12 may be formed from one or more tubular bodies, e.g., having variable flexibility along its length. For example, the distal end 16 may be substantially flexible to facilitate introduction through tortuous anatomy, e.g., terminating in a rounded, tapered, and/or other substantially atraumatic distal tip 17. The distal end 16 may be sized and/or shaped for introduction into a body lumen, e.g., having a diameter between about one and seven millimeters (1-7 mm), or less than 1.7 millimeters. The proximal end 14 may be substantially flexible, semi-rigid, or rigid, e.g., having sufficient column strength to facilitate advancing the distal end 16 through a patient's vasculature by pushing on the proximal end 14. Optionally, a shaft support wire or other stiffener (not shown) may be provided within the proximal end 14, if desired, e.g., to facilitate pushing the catheter 12 from the proximal end 14. The catheter 12 may be formed from plastic, metal, or composite materials, e.g., a plastic material having a wire, braid, or coil core, which may preventing kinking or buckling of the catheter 12 during advancement.

As shown in FIG. 1, the catheter 12 may include a handle 50 on the proximal end 14, e.g., to facilitate manipulating the catheter 12. The handle 50 may include one or more ports 52 communicating with respective lumens 18 within the catheter 12, as described further below. The handle 50 may be molded, machined, or otherwise formed from plastic, metal, or composite material, e.g., providing an outer casing, which may be contoured or otherwise shaped to ease manipulation. The proximal end 14 of the catheter 12 may be attached to the handle 50, e.g., by bonding, cooperating connectors, interference fit, and the like. Optionally, if the apparatus 10 includes any actuatable components (not shown) on the distal end 16, the handle 50 may include one or more actuators (also not shown), such as one or more slides, dials, buttons, and the like, for actuating or otherwise manipulating the components from the proximal end 14.

In the exemplary embodiment shown in FIG. 1, the catheter 12 includes at least two lumens 18 extending between the proximal and distal ends 14, 16. For example, the catheter 12 may include an inflation lumen 18a that extend from port 52a in the handle 50 through the catheter 12 to an opening (not shown) that communicates with the interior of the balloon 20. The port 52a on the handle 50 may include a connector, e.g., a luer lock connector (not shown), one or more seals (also not shown), and the like. A source of inflation media and/or vacuum, e.g., a syringe (not shown) filled with saline or other inflation media, may be connected to the port 52a, e.g., directly or via tubing (also not shown), for expanding and/or collapsing the balloon 20.

In addition, the catheter 12 may include an instrument lumen 18b that extends from port 52b in the handle 50 to an opening 17a in the distal tip 17. The instrument lumen 18b may have sufficient size to allow a guidewire or other rail or instrument (not shown) to be inserted therethrough, e.g., to facilitate advancing the catheter 12 over the rail, as explained further below. The handle 50 may include one or more seals (also not shown) that prevent fluid, e.g., blood, from flowing proximally out of the port 52b, yet allow one or more instruments to be inserted therethrough and into the instrument lumen 18b. Alternatively, a "rapid exchange" instrument lumen may be provided instead of lumen 18b that extends from a side port (not shown) at an intermediate location on the catheter 12 to the opening 17a. The lumens 18a, 18b may be disposed adjacent one another or, alternatively, in concentric or other arrangements within the body of the catheter 12, e.g., along the entire length of the catheter 12 or having different arrangements at different locations, as desired.

With continued reference to FIG. 1, the balloon 20 generally includes a first or proximal region 20a and a second or distal region 20b. Generally, when fully inflated, the proximal region 20a of the balloon 20 may expand to a bulbous or other shape and the distal region 20b may expand to a substantially uniform cylindrical shape, e.g., having a diameter smaller than the proximal region 20a, as described further elsewhere herein.

With additional reference to FIGS. 2A and 2B, the balloon 20 may include a first membrane or layer 22 including proximal and distal ends 24, 26 bonded or otherwise secured to the distal end 16 of the catheter 12, e.g., by bonding with adhesive, sonic welding, using an annular collar or sleeve, and the like. In addition, the balloon 20 also includes a second membrane or layer 32, e.g., bonded or otherwise attached to the first membrane 22.

In the exemplary embodiment shown in FIGS. 2A and 2B, the first membrane 22 may be formed from compliant or semi-compliant polymeric or other plastic material, e.g., polyethylene, polyurethane, nylon, silicone, low to mid durometer PEBAX, and the like, using conventional methods, such as blow molding, dip molding, and the like. The first membrane 22 may be formed into a desired shape, e.g., including tapered proximal and distal regions 25, 27 expanding from the proximal and distal ends 24, 26 to a central region 28. The central region 28 may have a substantially uniform diameter in a relaxed state, e.g., after molding from which the central region 28 may be expanded, e.g., during inflation of the balloon 20. Alternatively, as shown in FIG. 2C, the first membrane 22' may include a central region 28' including a first region 28a' proximal to a second region 28b.' The first and second regions 28a,' 28b' may have substantially uniform diameters with the first region 28a' having a larger diameter than the second region 28b,' e.g., having a difference in diameter of about one millimeter (1.0 mm). As shown, the first membrane 28 may include a proximal tapered region 25' transitioning from the first region 28a' to proximal end 24' and a distal tapered region 27' transitioning from the second region 28b' to distal end 26.' The first membrane 22 may have a substantially uniform wall thickness, e.g., between the proximal and distal ends 24, 26 or the wall thickness may vary, e.g., being thinner in a proximal region than distal region (e.g., corresponding to the first and second regions 28a,' 28b' shown in FIG. 2C), if desired.

The second membrane 32 may be formed from substantially inelastic polymeric or plastic material, e.g., PET, nylon, mid to high durometer PEBAX, and the like, or may be formed from substantially elastic material, e.g., silicone, polyurethane, or polyethylene, such that the balloon 20 may be expanded to a variety of sizes depending upon the volume and/or pressure of fluid within the interior. The second membrane 32 may have a substantially cylindrical shape between its proximal and distal ends 34, 36, e.g., having a substantially uniform diameter and/or wall thickness in a relaxed state.

During fabrication, the first and second membranes 22, 32 may be formed separately, e.g., by blow molding, dip molding, and the like, and then the second membrane 32 may be attached to the central portion 28 of the first membrane 22, e.g., to define the second region 20b of the balloon 20. As best seen in FIG. 2B, the second membrane 32 may have a length shorter than the central region 28 of the first membrane 22. For example, the second membrane 32 may be positioned over the central region 28 immediately adjacent the distal tapered region 27 such that a portion of the central region 28 remains uncovered between the second membrane 32 and the proximal tapered region 25, i.e., to provide the first region 20a of the balloon 20. Once positioned over the central region 28, the second membrane 32 may be attached to the outer surface of the first membrane 22, e.g., by bonding with adhesive, sonic welding, fusing, and the like substantially continuously or intermittently to the outer surface. Alternatively, the second membrane 32 may be attached to an inner surface of the central region 28 of the first membrane (not shown).

In another alternative, the second membrane 32 may be formed directly on the central region 28 of the first membrane 22. For example, material for the second membrane 32 may be coated onto the first membrane 22, e.g., by dip coating or spray coating. For example, with the first membrane 22 on a mandrel or inflated to open the first membrane 22, the central region 28 may be dipped into material sufficient distance to cover the desired length of the central region 28 with the material. In exemplary embodiments, the material may be same material used to form the first membrane 22 or may be a slightly stronger and/or less compliant material.

In one embodiment, the second membrane 32 may be formed from semi-compliant or non-compliant material, e.g., having a lower elasticity than the material of the first membrane 22. Alternatively, the first and second membranes 22, 32 may be formed from the same material, e.g., compliant or semi-compliant material, e.g., having substantially the same thickness as the first membrane 28. Alternatively, the second membrane 32 may be formed from the same base material as the first membrane 22 but having different mechanical properties, e.g., having a greater thickness than the first membrane 22, having reinforcement elements embedded therein (not shown), and the like.

In exemplary embodiments, the first region 20a may have a length between about six and sixteen millimeters (6.0-16.0 mm), while the second region 20b may have a length between about 5.5 and 13.5 millimeters, e.g., between 11.5-13.5 mm. In addition or alternative, the first region 20a may have a diameter in a relaxed state (i.e., upon fabrication before full inflation) between about four and eight millimeters (4.0-8.0 mm) and the second region 20b may have a diameter between about three and seven millimeters (3.0-7.0 mm).

Returning to FIG. 1, the resulting balloon 20 may be attached to the distal end 16 of the catheter 12, e.g., by attaching the distal end 26 adjacent the distal tip 17 and attaching the proximal end 24 to the distal end 16 proximal to the distal tip 17. As shown in FIG. 1, the reinforced second region 20b is located distal to the first region 20a, i.e., closer to the distal tip 17 of the catheter 12. Alternatively, in some applications, the orientation of the first and second regions 20a, 20b may be reversed, i.e., with the reinforced second region 20b proximal to the first region 20a. The balloon 20 may be rolled, folded, or otherwise compressed over the distal end 16 of the balloon 20, e.g., to provide a delivery condition for introduction into a patient's body as shown in FIG. 2D. Additional information regarding methods and/or materials for making the balloon 20 and/or catheter 12 may be found in U.S. Pat. Nos. 7,582,111, 7,862,601, and 9,034,025, the entire disclosures of which are expressly incorporated by reference herein.

Because of the resulting difference in mechanical properties of the first and second regions 20a, 20b, the balloon 20 may expand into different diameters and/or shapes when inflated. For example, due to the compliance of the first membrane material and the single layer of material for the first region 20a, the first region 20a of the balloon 20 may be expanded greater than the relaxed molded shape, e.g., with the amount of expansion proportional to the volume and/or pressure of fluid introduced into the interior of the balloon 20. In contrast, given the additional support provided by the second membrane 32, the second region 20b of the balloon 20 may expand to a predetermined cylindrical diameter smaller than the maximum expanded size of the first region 20a.

For example, if the balloon 20 is inflated to an initial pressure between about three and five atmospheres (3-5 ATM), both the first and second regions 20a, 20b may expand substantially simultaneously (i.e., with minimal delay between one region and the other), e.g., to engage a prosthesis within which the balloon 20 is positioned, as described further below. Thereafter, the pressure may be increased further, e.g., to a maximum pressure between about eight and twenty atmospheres (8-20 ATM), whereupon the second region 20b may resist further expansion, while the first region 20a continues to expand, e.g., to flare or otherwise shape the prosthesis, also as described further below. For example, with an initial diameter between about 4-8 mm, the first region 20a may expand into a substantially spherical shape having a maximum outer diameter of between about 9.0-12.5 mm when exposed to the maximum pressure.

Figure 6:
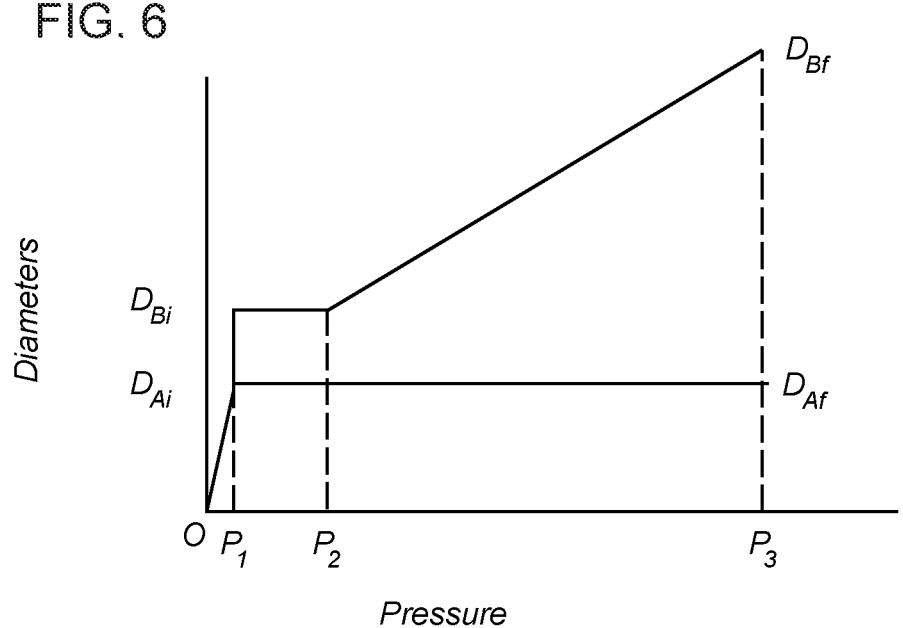
FIG. 6 is a graph showing an exemplary expansion profile of unreinforced and reinforced regions of a balloon relative to internal pressure within the balloon.

FIG. 6 shows an exemplary expansion profile that may be experienced by the balloon 20 as inflation media is introduced into the interior of the balloon 20. As the pressure increases from 0 to P1, the first and second regions 20a, 20b may rapidly expand to the their formed (e.g., molded) diameters, e.g., with the second region 20b expanding to diameter Dai and the first region 20a expanding to diameter Dbi. As the pressure is increased further, the diameters of the first and second regions 20a, 20b may remain substantially constant as the balloon 20 pressurizes. Once the balloon 20 reaches a threshold pressure P2 ("the cracking pressure"), further inflation causes the first region 20a to expand further while the second region 20b remains at substantially the same diameter (e.g., Daf=Dai). The first region 20a may continue to expand as additional pressure is applied, e.g., until a desired final pressure P3 and diameter Dbf are achieved.

Figure 7:
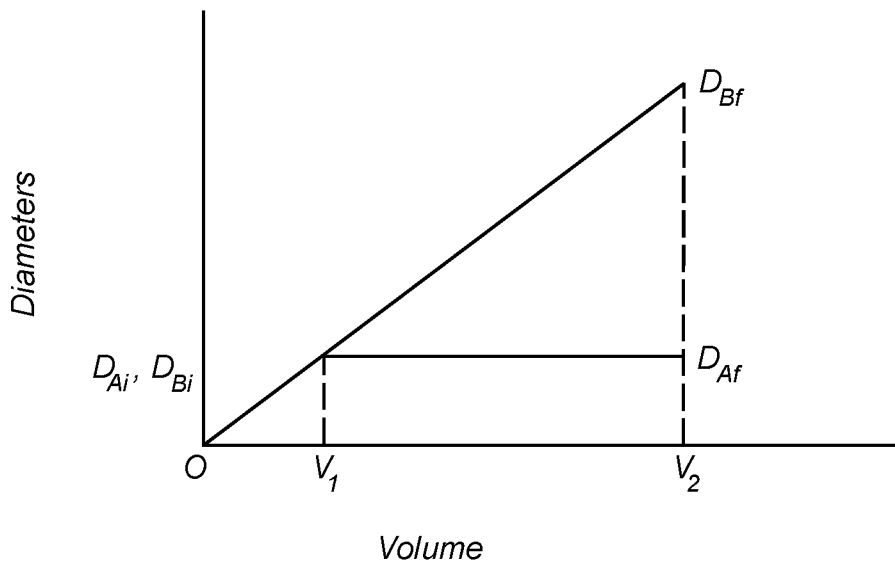
FIG. 7 is a graph showing an exemplary expansion profile of unreinforced and reinforced regions of a balloon relative to internal volume of inflation media within the balloon.

FIG. 7 shows another exemplary expansion profile that may be experienced by the balloon 20 based on volume of fluid introduced into the interior of the balloon 20 (rather than based on internal pressure, as shown in FIG. 6). In this embodiment, as the volume within the balloon 20 increases from 0 to V1 ("the cracking volume"), the first and second regions 20a, 20b may expand substantially simultaneously, e.g., to their formed diameters Dai, Dbi. If additional inflation media is introduced beyond V1, the first region 20a may expand further, e.g., to Dbf, while the second region 20b remains substantially the same (e.g., Daf=Dai).

Optionally, one or more outer surfaces, e.g., the outer surface 38 of the second membrane 32 and/or the outer surface 29a of the first membrane 22 defining the first region 20a of the balloon 20 may include one or more features thereon for enhancing traction, friction, or other engagement with structures, e.g., a stent, prosthetic valve, or other prosthesis (not shown) contacted by the balloon 20 when expanded. For example, the outer surface 38 of the second region 20b of the balloon 20 may be treated or textured, may include ribs or other protrusions, and the like (not shown) to increase friction or other engagement upon expansion.

Optionally, the balloon 20 may include one or more diagnostic and/or therapeutic elements. For example, in one embodiment, the outer surfaces 29a, 38 may carry one or more therapeutic agents, which may be pressed against the wall of a vessel, e.g., at an ostium, lesion, or within a branch, as described further elsewhere in the applications incorporated by reference herein. In another embodiment, one or more electrodes, ultrasound elements, or other components (not shown) may be provided on the balloon for delivering energy to tissue contacted by the balloon 20.

Turning to FIGS. 3A-3F, an exemplary method is shown for using the apparatus 10 to flare and/or otherwise expand a stent 40 deployed within a patient's body, e.g., including an ostium 90. As shown, the ostium 90 may be an opening in a wall of a first or main body lumen or trunk 92 that communicates with a second body lumen or branch 94. In exemplary embodiments, the main body lumen 92 may be the ascending or descending aorta, and the branch body lumen may be a coronary artery, a common carotid artery, or a peripheral artery. A stenosis, occlusion, or other lesion 96 may exist at and/or adjacent to the ostium 90, e.g., extending at least partially into the branch 94. The lesion 96 may include atherosclerotic plaque or other material that partially or completely occludes blood or other fluid flow between the trunk 92 and the branch 94.

Figure 3A:
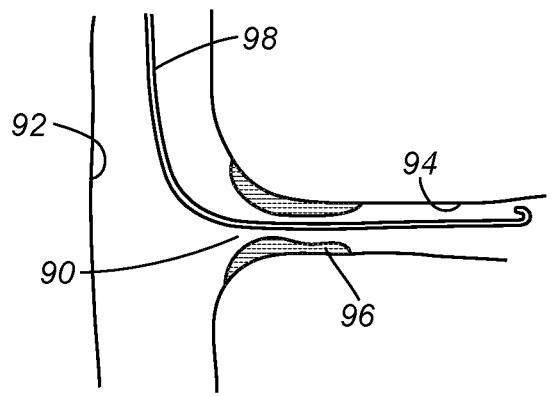
FIGS. 3A-3F are cross-sectional views of a patient's body including an ostium communicating between a main vessel and a branch vessel, showing a method for flaring a stent previously deployed within the branch vessel using the apparatus of FIG. 1.

Initially, as shown in FIG. 3A, a guidewire 98 or other rail may be introduced from the trunk 92 through the ostium 90 into the branch 94, e.g., using conventional methods. For example, a percutaneous puncture or cut-down may be created at a peripheral location (not shown), such as a femoral artery, carotid artery, or other entry site, and the guidewire 98 may be advanced through the patient's vasculature from the entry site, e.g., alone or with the aid of a guide catheter (not shown). For example, a distal end of a guide catheter (not shown) may be advanced over the guidewire 98 into the trunk 92, e.g., until the distal end is disposed adjacent or proximal to the ostium 90. The guide catheter may be used to advance one or more instruments (such as any of the catheters or other devices described herein) over the guidewire 98 and into the trunk 92 and/or branch 94.

If the lesion 96 completely occludes the branch 94, the guidewire 98 may be directed through the occlusion, or other devices (not shown) may be advanced over the guidewire 98 or otherwise in conjunction with the guidewire 98 to create a passage through the lesion 96 for the guidewire 98, e.g., using conventional methods.

After the guidewire 98 is directed into the branch 94 beyond the lesion 96, it may be desirable to at least partially dilate the lesion 96. For example, an angioplasty catheter (not shown) may be advanced through the guide catheter and/or over the guidewire 98 into and through the lesion 96, whereupon a balloon or other element on the catheter may be expanded to at least partially dilate the lesion 96. If desired, other procedures may also be performed at the lesion 96, e.g., to soften, remove, or otherwise treat plaque or other material forming the lesion 96, before the stent 40 is implanted. After completing any such procedures, any instruments advanced over the guidewire 98 may be removed.

Figure 3B:
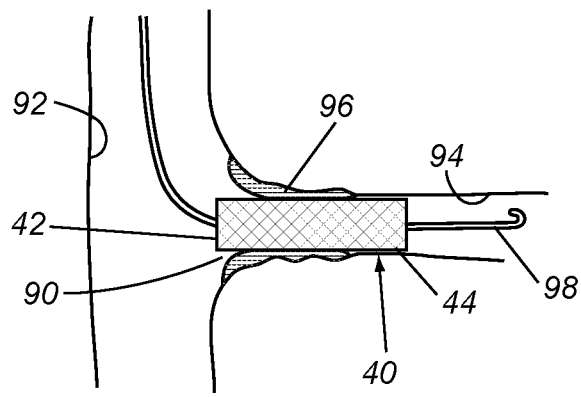

To deliver the stent 40, any delivery catheter and/or conventional procedure may be used. For example, a distal end of a delivery catheter (not shown) may be advanced over the guidewire 98 and/or through the guide catheter from the entry site into the trunk 92. For example, with the distal end of the guide catheter against or adjacent the ostium 90, the distal end of the delivery catheter may be advanced from the guide catheter, through the ostium 90, and into the branch 94. The delivery catheter may be positioned such that the stent 40 extends into and through the lesion 96 and/or branch 94. The stent 40 may be expanded and/or otherwise deployed from the delivery catheter to place the stent 40 across the lesion 96 and/or within the branch 94, e.g., using conventional methods. For example, as shown in FIG. 3B, the stent 40 may be deployed such that a first end 42 of the stent 40 extends at least partially into the ostium 90 and/or the trunk 92, and a second end 44 of the stent 40 is disposed within the branch 94 beyond the lesion 96.

As shown, the stent 40 may have a substantially uniform diameter cross-section once deployed. For example, the stent 40 may be expanded to dilate and/or otherwise engage the lesion 96 and/or branch 94. Alternatively, the stent 40 may be partially expanded using the delivery catheter, allowing the stent 40 to be further expanded by the apparatus 10, as described below.

Figure 3C:
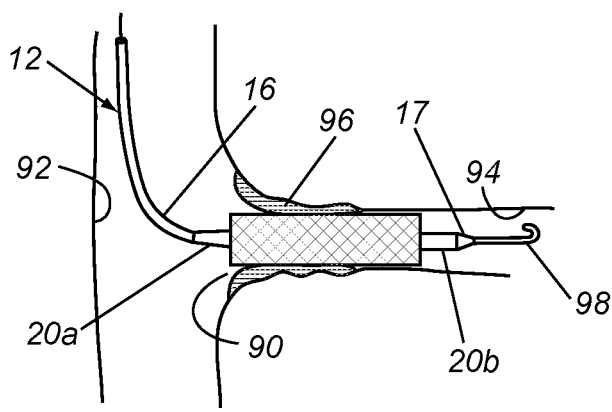

Turning to FIG. 3C, thereafter, the distal end 16 of the catheter 12 (with the balloon 20 in its contracted condition) may be introduced into the trunk 92 to flare and/or otherwise expand the stent 40. For example, the delivery catheter may be removed, and the distal end 16 of the catheter 12 may be advanced over the same guidewire 98 into the trunk 92. In the embodiment shown in FIG. 1, a proximal end (not shown) of the guidewire 98 may be backloaded into the opening 17a through the instrument lumen 18b and out the port 52b. The distal end 16 may then be advanced over the guidewire 98 into the patient's body over the guidewire 98.

As shown in FIG. 3C, the distal end 16 may be advanced through the stent 40 and ostium 90 at least partially into the branch 94. For example, the distal end 16 may be positioned such that the second region 20b of the balloon 20 is positioned within and/or beyond the stent 40, e.g., beyond the first end 42, and the first region 20a of the balloon 20 is positioned adjacent the ostium 90, e.g., within and/or proximal to the first end 42 of the stent.

Optionally, to facilitate positioning, the catheter 12 may be monitored using fluoroscopy or other external imaging, e.g., to observe and monitor markers (not shown) on the distal end 16. For example, markers may be located on the distal end 16 to identify the ends of the first and second regions 20a, 20b of the balloon 20. Thus, using the markers, the second region 20b may be aligned with the distal end 44 and/or portion of the stent 40 within the branch 94 beyond the ostium 90 and the first region 20a may be aligned with the first end 42 of the stent 40 and/or the ostium 90, as desired.

Figure 3D:
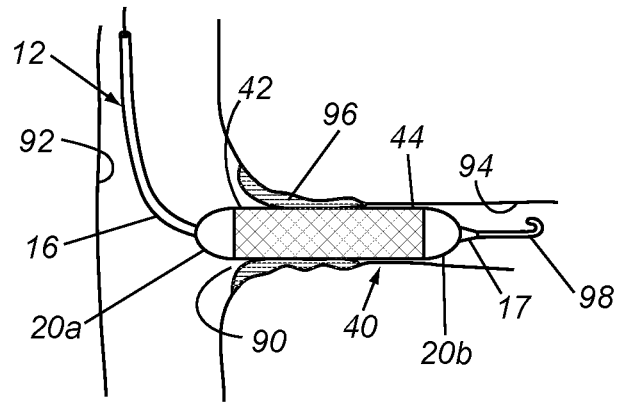

Turning to FIG. 3D, with the catheter 12 positioned as desired, the balloon 20 may be expanded, e.g., by coupling a syringe or other device (not shown) to port 52a (not shown in FIG. 3D, see FIG. 1) and delivering saline or other inflation media into the interior of the balloon 20 via inflation lumen 18a, to engage the stent 40 and/or wall of the branch 94. For example, when inflated to an initial pressure, both the first and second regions 20a, 20b of the balloon 20 may expand substantially simultaneously to similar diameters to engage both the stent 40 and the wall of the branch 94 beyond the stent 40 to prevent substantial axial migration of the stent 40.

Figure 3E:
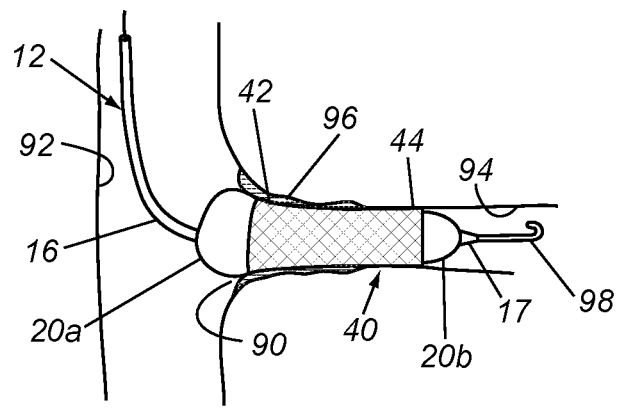

Thereafter, as shown in FIG. 3E, the balloon 20 may be inflated further, e.g., by delivering additional inflation media into the interior to a higher pressure to expand the first region 20a to flare the stent 40. For example, as the first region 20a expands further, the first end 42 of the stent 40 is expanded, e.g., into a flared configuration, which may conform to the shape of the first region 20a and/or the ostium 90.

With the stent 40 sufficiently engaged by the initial inflation, the stent 40 and catheter 12 may remain substantially stationary during the subsequent inflation and flaring. Otherwise, without the second region 20b engaging the stent 40 and wall of the branch 94, there may be a tendency for the stent 40 to migrate distally into the branch 94 rather than flaring in place, e.g., maintaining its substantially uniform diameter, which may shear or otherwise remove material from the lesion 96 and/or wall of the branch 94 and potentially release the material within the branch 94. In addition or alternatively, without the second region 20b expanded, there may be a tendency of the distal end 16 of the catheter 12 to move proximally away from the stent 40 and ostium 90. Thus, the second region 20b may provide an anchor that ensures the first end 42 of the stent 40 is flared in a desired manner with the stent 40 and catheter 12 substantially fixed relative to one another and the ostium 90.

Figure 3F:
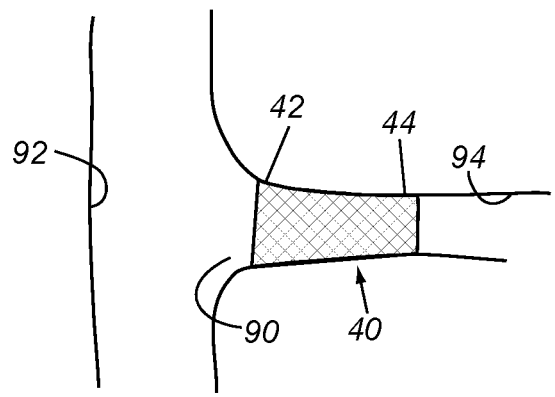

With the stent 40 fully deployed, the balloon 20 may be deflated or otherwise collapsed, and the catheter 12 may be withdrawn from the branch 94 and trunk 92, and from the patient's body, e.g., into the guide catheter (not shown). The guide catheter and/or guidewire 98 may then be removed from the patient's body, leaving the stent 40 in place, as shown in FIG. 3F. One advantage of the first region 20a expanding elastically beyond the second region 20b during final inflation is that the tensile forces in the first region 20a may generate elastic recoil as inflation media is removed from the balloon 20. Thus, as the balloon 20 is deflated, the first region 20a may collapse quickly, which may reduce over deflation time for the balloon 20 before the catheter 12 can be removed.

In other alternatives, the apparatus and methods herein may be used for treating and/or delivering other structures within a patient's body. For example, turning to FIG. 4, another embodiment of a balloon apparatus 110 is shown that includes a catheter 112 including a distal end 116 carrying a balloon 120 having a reinforced central region 120b between two unreinforced outer regions 120a. The balloon 120 may be constructed similar to the previous embodiments from a first membrane 222 including first and second ends 224, 226 and a central region 228 reinforced partially by a second membrane 232 to define the reinforced central region 220b.

Figure 5A:
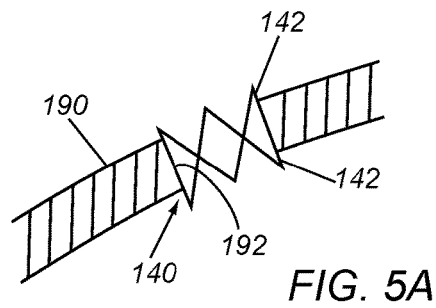
FIGS. 5A-5C are cross-sectional views of a patient's body showing an exemplary method for expanding a prosthetic heart valve implanted within a site of a native valve that has been replaced.
Figure 5B:
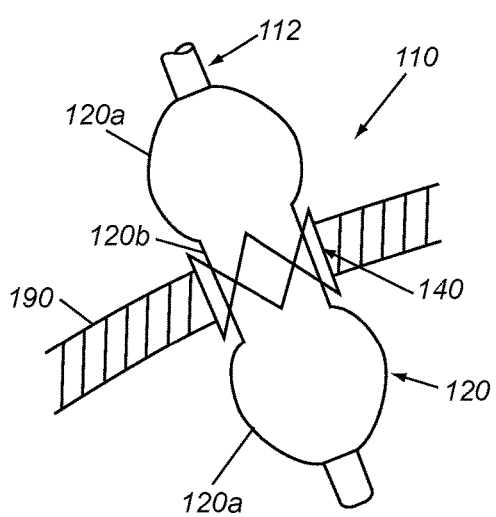
Figure 5C:
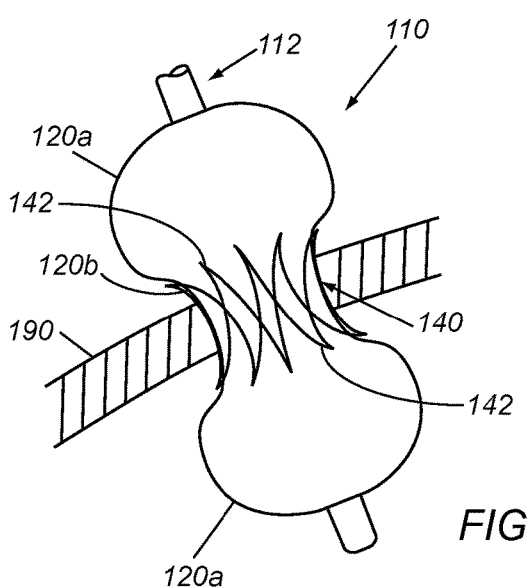

In an exemplary embodiment, shown in FIGS. 5A-5C, during use, the balloon 220 may be used to flare ends of a prosthesis, e.g., a prosthetic heart valve, stent, or other cylindrical prosthesis 140. As shown in FIG. 5A, a prosthetic valve prosthesis 140 has been deployed within an annulus 192, e.g., the site of an aortic valve that has been replaced within a patient's heart 190. The prosthesis 140 may include a frame defining first and second ends 142, 144 and supporting one or more leaflets or other valve elements (not shown).

Turning to FIG. 5B, the distal end 116 of the catheter 112 may be introduced the patient's body with the balloon 120 deflated, e.g., from a percutaneous entry site into the patient's vasculature and advanced into the aorta adjacent the annulus 192. The catheter 112 may be advanced to position the balloon 120 through the prosthesis 140 across the annulus 192, e.g., positioning the reinforced central region 128b within the frame of the prosthesis 140. The central region 128b may have a length longer than the prosthesis 140, e.g., to provide a transition region at the ends 142, 144 of the prosthesis 140, or may have a length shorter than the prosthesis 140, as desired.

Once properly positioned, the balloon 120 may be inflated to an initial pressure, e.g., between one and two atmospheres (1.0-2.0 ATM), whereupon both the outer regions 128a and central region 128b expand substantially simultaneously, e.g., such that the central region 128b engages the frame of the prosthesis 140 to lock relative positioning of the balloon 120 and prosthesis 140, as shown in FIG. 5B. Optionally, the diameter of the central region 128b may be slightly larger than the deployed diameter of the prosthesis 140, e.g., such that the prosthesis 140 is expanded further upon initial inflation of the balloon 120.

Thereafter, the balloon may be inflated further, e.g., to pressures greater than five or six atmospheres, thereby causing the unreinforced outer regions 128a to expand further, while the central region 128b resists further expansion. In this manner, the ends 142, 144 of the prosthesis 140 may be flared outwardly, as shown in FIG. 5C, e.g., to create a flange or other shape that secures the prosthesis 140 within the annulus 192 without expanding and/or risking damage to the central region of the prosthesis 140 (e.g., which may carry leaflets and/or other less durable components). Thus, the flared ends 142, 144 may resist subsequent migration of the prosthesis 140. In addition, the flared ends 142, 144 may provide one or more other advantages, e.g., reduce the risk of thrombus formation, e.g., to minimize exposure of bare metal on the prosthesis 140, engage the ends 142, 144 into adjacent tissue to promote endotheliazation, and the like.

Once the prosthesis 140 is dilated and/or flared sufficiently, the balloon 120 may be deflated, and the catheter 112 removed from the annulus 192 and the patient's body.

Figure 4:
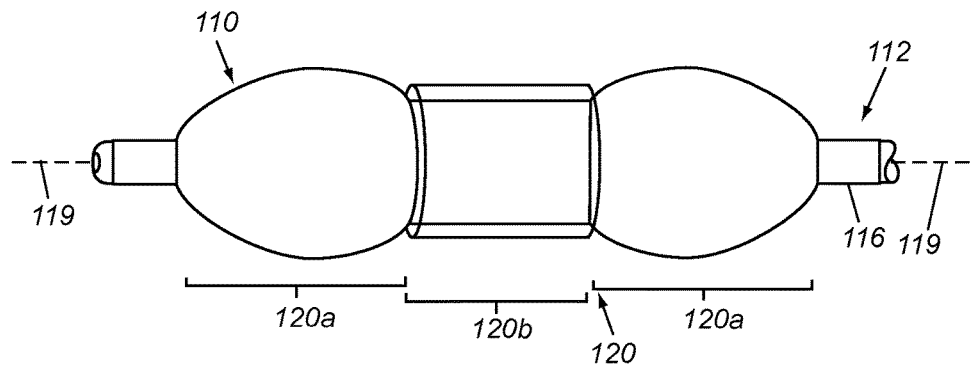
FIG. 4 is a side view of another exemplary embodiment of a catheter including a balloon having a reinforced central region to control expansion of the balloon.

In other embodiments, the catheter 112 and balloon 120 shown in FIG. 4 may be used for other procedures. For example, tracheal and/or esophageal stents often include flared ends, and the balloon 120 may be positioned across such a deployed stent to further flare and/or shape the stent. Similarly, the balloon 120 may be used to flare ends of a stent deployed within a pulmonary artery, a urinary or digestive tract, or other body lumen. The balloon 120 may allow the ends of such stents to be flared substantially simultaneously, thereby simplifying delivery of such stents compared to conventional methods.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for flaring a stent, comprising:
a tubular member comprising a proximal end, a distal end sized for introduction into a patient's body, and one or more lumens extending therebetween; and
a balloon carried on the distal end comprising:
a first membrane including first and second ends attached to the distal end, and a central region extending between first and second tapered regions transitioning to the first and second ends, respectively; and
a second membrane surrounding the central region from the second tapered region partially towards the first tapered region to define a reinforced region of the balloon,
wherein the first membrane is formed from elastic material and the second membrane is formed from material having an elasticity equal to or less than the first membrane, and
wherein the first and second membranes define a first diameter in a relaxed, formed state, and
wherein the material of the first and second membranes are configured such that, upon inflation of the balloon to a first pressure, the first and second membranes expand substantially simultaneously from a delivery condition to the first diameter, and, upon inflation of the balloon beyond the first pressure, the reinforced region of the balloon remains at the first diameter and the rest of the central portion of the first membrane continues to expand to a diameter greater than the first diameter.

2. The apparatus of claim 1, wherein the first and second membranes are formed from the same material.

3. The apparatus of claim 2, wherein the first and second membranes have the same thickness.

4. The apparatus of claim 1, wherein the second membrane is formed from inelastic material.

5. The apparatus of claim 1, wherein the second membrane is attached over an outer surface of the central region.

6. The apparatus of claim 5, wherein the second membrane is attached substantially continuously over the outer surface by at least one of bonding, fusing, and sonic welding.

7. The apparatus of claim 1, wherein the second membrane is formed over the central region by one of dip molding and spray molding.

8. The apparatus of claim 1, wherein a portion of the first membrane adjacent the reinforced region is molded into a shape configured to expand to a bulbous shape when expanded to a diameter greater than the first diameter.

9. An apparatus for flaring a stent, comprising:
a tubular member comprising a proximal end, a distal end sized for introduction into a patient's body, and one or more lumens extending therebetween; and
a balloon carried on the distal end comprising:
a first membrane including first and second ends attached to the distal end, and a central region extending between first and second tapered regions transitioning to the first and second ends, respectively; and
a second membrane surrounding the central region from the second tapered region partially towards the first tapered region to define a reinforced region of the balloon configured to expand to a substantially uniform diameter cylindrical shape,
wherein the first membrane is formed from elastic material and the second membrane is formed from material having an elasticity equal to or less than the first membrane such that the first membrane between the second membrane and the first tapered region expands to a bulbous shape larger than the reinforced region when expanded.

10. The apparatus of claim 9, wherein the first and second membranes are formed from the same material.

11. The apparatus of claim 10, wherein the first and second membranes have the same thickness.

12. The apparatus of claim 9, wherein the second membrane is formed from inelastic material.

13. The apparatus of claim 9, wherein the second membrane is attached over an outer surface of the central region.

14. The apparatus of claim 13, wherein the second membrane is attached substantially continuously over the outer surface by at least one of bonding, fusing, and sonic welding.

15. The apparatus of claim 9, wherein the first and second membranes define a first diameter in a relaxed, formed state.

16. The apparatus of claim 15, wherein the material of the first and second membranes are configured such that, upon inflation of the balloon to a first pressure, the first and second membranes expand substantially simultaneously from a delivery condition to the first diameter, and, upon inflation of the balloon beyond the first pressure, the reinforced region of the balloon remains at the first diameter and the rest of the central portion of the first membrane continues to expand to a diameter greater than the first diameter.

\* \* \* \* \*